(12) United States Patent  (10) Patent No.: US 8,228,058 B2
Nishimizu et al.  (45) Date of Patent: Jul. 24, 2012

(54) EDDY CURRENT FLAW DETECTION PROBE

(75) Inventors: Akira Nishimizu, Tokai (JP); Hirofumi Ouchi, Hitachi (JP); Yoshio Nonaka, Hitachi (JP); Yosuke Takatori, Hitachi (JP); Akihiro Taki, Hitachi (JP); Makoto Senoo, Tokai (JP)

(73) Assignee: Hitachi-GE Nuclear Energy, Ltd., Ibaraki (JP)

( * ) Notice: Subject to any disclaimer, the term of this patent is extended or adjusted under 35 U.S.C. 154(b) by 677 days.

(21) Appl. No.: 12/128,316

(22) Filed: May 28, 2008

(65) Prior Publication Data

US 2009/0009162 A1 Jan. 8, 2009

(30) Foreign Application Priority Data

May 29, 2007 (JP) ................................. 2007-142428

(51) Int. Cl.
*G01R 33/02* (2006.01)
*G01N 27/82* (2006.01)

(52) U.S. Cl. ........ 324/238; 324/222; 324/239; 324/240; 702/38

(58) Field of Classification Search .......... 324/228–262; 702/38
See application file for complete search history.

(56) References Cited

U.S. PATENT DOCUMENTS

| 4,495,466 | A | * | 1/1985 | Lakin ............................. 324/242 |
| 6,670,808 | B2 | * | 12/2003 | Nath et al. .................... 324/230 |
| 7,235,967 | B2 | | 6/2007 | Nishimizu et al. |
| 2003/0025496 | A1 | * | 2/2003 | Trantow et al. ............... 324/219 |
| 2005/0062470 | A1 | * | 3/2005 | Shoji ............................. 324/240 |
| 2006/0170420 | A1 | * | 8/2006 | Nishimizu et al. ............ 324/239 |
| 2008/0004817 | A1 | | 1/2008 | Nishimizu et al. |

FOREIGN PATENT DOCUMENTS

| JP | 2003-344360 | 12/2003 |
| JP | 2006-194661 | 7/2006 |
| JP | 2006-300791 | 11/2006 |

* cited by examiner

*Primary Examiner* — Huy Q Phan
*Assistant Examiner* — Emily Chan
(74) *Attorney, Agent, or Firm* — Brundidge & Stanger, P.C.

(57) ABSTRACT

Disclosed is an eddy current flaw detection probe that is capable of pressing itself against an inspection target whose curvature varies. A flaw sensor is configured by fastening a plurality of coils to a flexible substrate that faces the surface of the inspection target. A first elastic body is positioned opposite the inspection target for the flaw sensor, is obtained by stacking two or more elastic plates, and has an elastic coefficient that varies in a longitudinal direction. A second elastic body is a porous body positioned between the flexible substrate and the first elastic body. A pressure section is employed to press the first elastic body toward the inspection target.

3 Claims, 16 Drawing Sheets

ONE LEAF SPRING
ELASTIC COEFFICIENT 1

TWO LEAF SPRINGS
ELASTIC COEFFICIENT 2

THREE LEAF SPRINGS
ELASTIC COEFFICIENT 3

EDDY CURRENT FLAW DETECTION PROBE

BACKGROUND OF THE INVENTION

1. Field of the Invention

The present invention relates to an eddy current flaw detection probe, and more particularly to an eddy current flaw detection probe that detects a flaw in an inspection target by sequentially selecting one of a plurality of coils and detecting a flaw detection signal from a detection coil.

2. Description of the Related Art

Some known eddy current flaw detection probes for detecting a flaw in an inspection target by sequentially selecting one of a plurality of coils (included in a multiple coil) and detecting a flaw detection signal from a detection coil employ a plurality of coils arranged on a flexible substrate, press the coils against the surface of an inspection target by using the elasticity, for instance, of a leaf spring, sequentially select one of the plurality of coils, and achieve flaw detection by detecting a flaw detection signal from a detection coil (refer, for instance, to JP-A-2006-194661 and JP-A-2003-344360).

SUMMARY OF THE INVENTION

For eddy current flaw detection based on the use of a multiple coil, it is important that a constant distance (lift-off) be maintained between the coil and the inspection target. To achieve such a purpose, the eddy current flaw detection probe disclosed in JP-A-2006-194661 uses a Bakelite or other similar rigid body prepared to fit the curvature of an inspection section as an elastic body positioned opposite an inspection target for the probe. Therefore, curvature changes can be handled as far as they can be absorbed by the elastic body. However, when a significant curvature change is encountered, it is necessary to change the Bakelite or other similar rigid body. This causes the inspection time to increase.

The eddy current flaw detection probe disclosed in JP-A-2003-344360 uses a sac-like object, which is positioned opposite an inspection target for the probe and filled with a gas, and a leaf spring or other similar elastic body. The sac-like object filled with a gas is structured so that the inner pressure within the sac-like object is used to generate a pressing force. However, if, for instance, the probe is used at a water depth of up to approximately 30 m for nuclear plant reactor inspection purposes, a great difference arises between the inner pressure of the sac-like object and the water pressure. Therefore, it is necessary to prepare a sac-like object appropriate for the water depth. Thus, a reactor inspection needs to be conducted while replacing the sac-like object in accordance with the water depth of the inspection target. This increases the inspection time. Further, if a leaf spring is used, the pressing force applied to an inspection target whose curvature varies becomes significantly uneven. This makes it difficult to maintain a constant lift-off. Consequently, inaccurate inspection results may be obtained.

It is an object of the present invention to provide an eddy current flaw detection probe that can be pressed against an inspection target whose curvature varies.

(1) In accomplishing the above object, according to one aspect of the present invention, there is provided an eddy current flaw detection probe having a flexible substrate, which faces the surface of an inspection target, and a plurality of coils, which are fastened to the flexible substrate and sequentially selectable. The eddy current flaw detection probe includes a first elastic body, a second elastic body, and pressure means. The first elastic body is positioned opposite the inspection target for the eddy current flaw detection probe and has an elastic coefficient that varies in a longitudinal direction. The second elastic body is a porous body positioned between the flexible substrate and the first elastic body. The pressure means presses the first and second elastic bodies against the inspection target.

The use of the above configuration makes it possible to press the probe against an inspection target whose curvature varies.

(2) According to another aspect of the present invention, there is provided the eddy current flaw detection probe as described in (1) above, wherein the first elastic body is made by stacking two or more elastic plates.

(3) According to another aspect of the present invention, there is provided the eddy current flaw detection probe as described in (2) above, wherein the second elastic body is sutured to the flexible substrate.

(4) According to another aspect of the present invention, there is provided the eddy current flaw detection probe as described in (1) above, wherein the pressure means includes a mechanism in which two or more elastic plates rotate relative to an axis orthogonal to a longitudinal direction.

(5) According to another aspect of the present invention, there is provided the eddy current flaw detection probe as described in (1) above, wherein the pressure means includes a mechanism in which two or more elastic plates rotate relative to an axis parallel to a longitudinal direction.

(6) According to still another aspect of the present invention, there is provided the eddy current flaw detection probe as described in (1) above, wherein the pressure means includes a mechanism that rotates relative to an axis perpendicular to two or more elastic bodies.

The present invention makes it possible to press the probe against an inspection target whose curvature varies.

DETAILED DESCRIPTION OF THE PREFERRED EMBODIMENTS

The configuration of an eddy current flaw detection probe according to a first embodiment of the present invention will now be described with reference to FIGS. 1 to 7.

First of all, the overall configuration of the eddy current flaw detection probe according to the first embodiment will be described with reference to FIG. 1.

Figure 1:
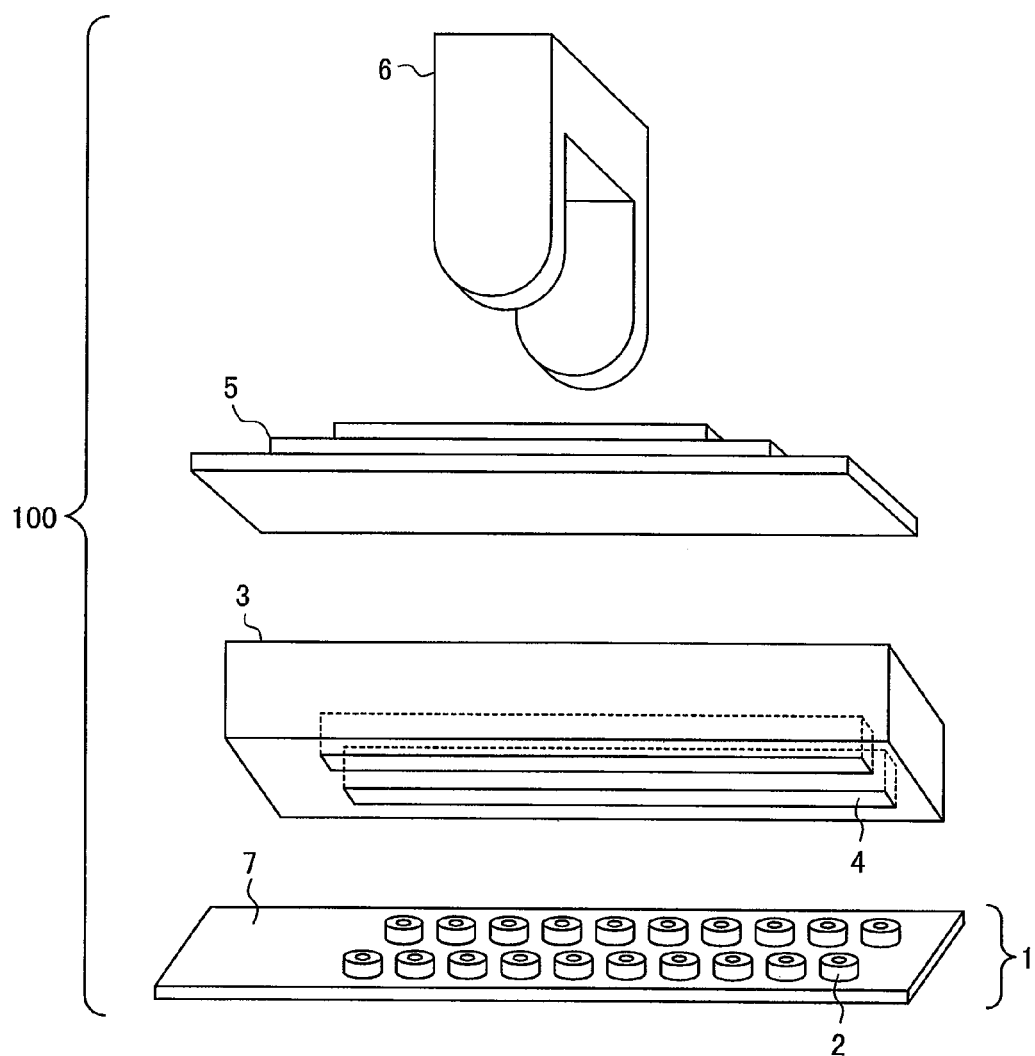
FIG. 1 is an exploded perspective view showing the overall configuration of an eddy current flaw detection probe according to a first embodiment of the present invention.

FIG. 1 is an exploded perspective view showing the overall configuration of the eddy current flaw detection probe according to the first embodiment of the present invention.

The eddy current flaw detection probe 100 includes a flaw sensor 1, which faces the surface of an inspection target; elastic bodies 3, 5, which bring the flaw sensor 1 into contact with the inspection target; and a pressure section 6, which presses the flaw sensor 1 against the inspection target via the elastic bodies 3, 5.

The flaw sensor 1 includes a flexible substrate 7, which is formed by stacking multiple layers of polyimide film or the like; and a plurality of coils 2, which are fastened to the non-inspection-target side of the flexible substrate 7 with adhesive or the like and unidirectionally arranged. In the present embodiment, the plurality of coils 2 are arranged to form two rows. The wiring (not shown) connected to each coil 2 is routed out of one end of the substrate (out of the left end in the example shown in the figure) by using a boundary between the layers of polyimide film.

One elastic body 3 is a porous body (sponge) made, for instance, of polyurethane rubber and shaped like a rectangular parallelepiped. It forms coil receiver grooves 4 that can receive two rows of coils 2 on the side facing the flexible substrate 7.

The other elastic body 5 does not permanently deform even when it is bent with the minimum curvature radius of the surface of an inspection target. For example, this elastic body 5 is a multilayer leaf spring that is formed by stacking a plurality of phosphor bronze plates or acrylic plates.

The pressure section 6 is made, for instance, of Bakelite or aluminum and used to press the flaw sensor 1 via the elastic bodies 3, 5. A concave section is formed at the center of the pressure section 6 and used to receive the flaw sensor 1 and elastic bodies 3, 5.

The flaw sensor 1, elastic bodies 3, 5, and pressure section 6 are formed into an assembly with adhesive, screws, engagement devices, or other known coupling devices to provide increased ease of handling. For example, the flexible substrate 7 of the flaw sensor 1 is glued to the elastic body 3. The elastic body 3 is glued to the elastic body 5. The flexible substrate 7 of the flaw sensor 1 is partially sutured to the elastic body 5 with an insulator (cotton) or the like. The elastic body 5 is screwed down to the pressure section 6.

When the eddy current flaw detection probe 100 is pressed against the surface of an inspection target, the multilayer leaf spring (elastic body 5) formed by stacking a plurality of plates works to bring the flaw sensor 1 into contact with the surface of the inspection target. The reason is that the elastic coefficient varies as the multilayer leaf spring is formed by stacking a plurality of plates. For example, the elastic body 5 is such that the elastic coefficient is high at the center where a large number of leaf spring plates are stacked and becomes lower toward the ends.

The operation of the multilayer leaf spring for use in the eddy current flaw detection probe according to the present embodiment will now be described with reference to FIGS. 2 to 7.

Figure 2A:
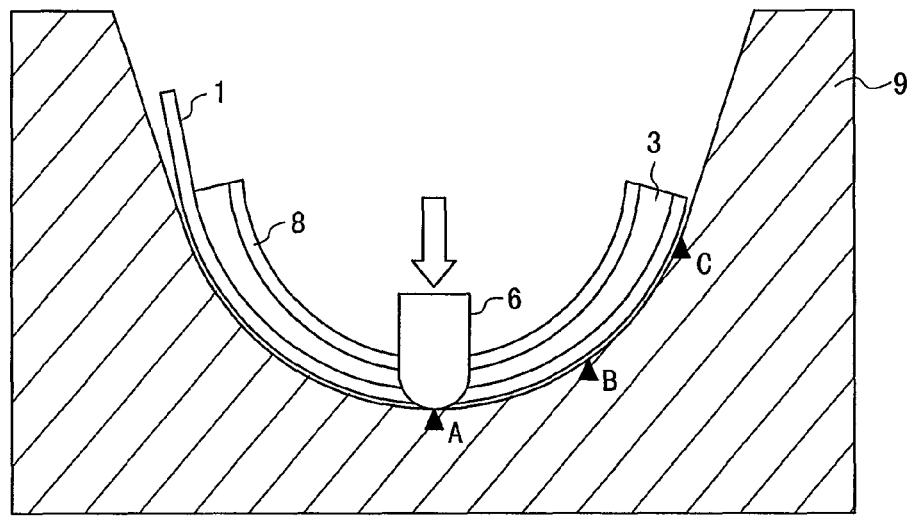
FIGS. 2A and 2B are side views showing the operation of a multilayer leaf spring for use in the eddy current flaw detection probe according to the first embodiment of the present invention.
Figure 2B:
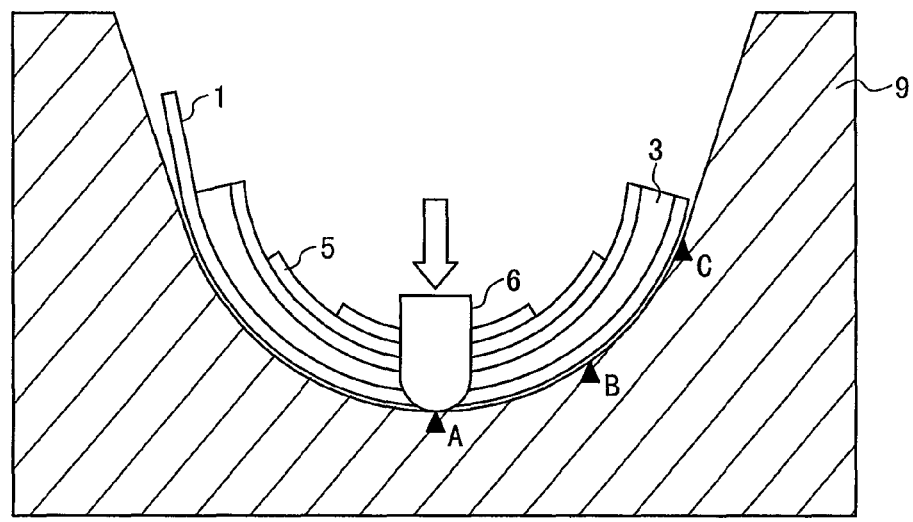
Figure 3:
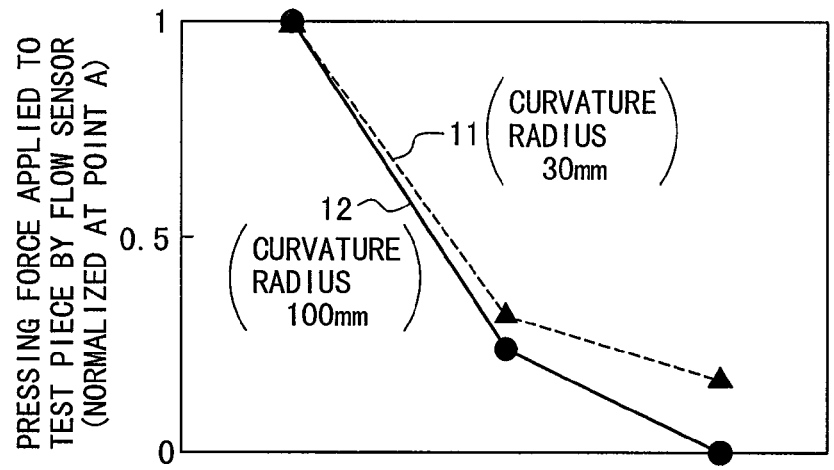
FIG. 3 is an illustration showing the pressing force applied during the use of a single-layer leaf spring as a comparative example.
Figure 4:
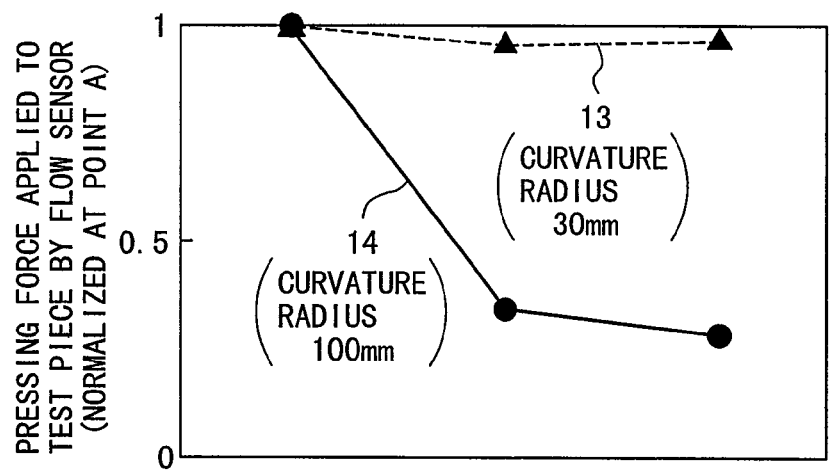
FIG. 4 is an illustration showing the pressing force applied by the multilayer leaf spring for use in the eddy current flaw detection probe according to the first embodiment of the present invention.

FIGS. 2A and 2B are side views showing the operation of the multilayer leaf spring for use in the eddy current flaw detection probe according to the first embodiment of the present invention. FIG. 2A is a side view showing an operation performed during the use of one leaf spring as a comparative example. FIG. 2B is a side view showing the operation of the multilayer leaf spring according to the present embodiment. Like elements in FIGS. 1, 2A, and 2B are identified by the same reference numerals. FIG. 3 is an illustration showing the pressing force applied during the use of one leaf spring as a comparative example. FIG. 4 is an illustration showing the pressing force applied by the multilayer leaf spring for use in the eddy current flaw detection probe according to the first embodiment of the present invention.

To achieve accurate flaw detection with the eddy current flaw detection probe 100, it is necessary to maintain a constant lift-off by pressing the entire surface of the flaw sensor 1 against the curved surface of an inspection target. The use of the elastic body 5, which is made of a multilayer leaf spring, makes it possible to press the entire surface of the flaw sensor 1 with a simple structure.

FIG. 2A is a schematic diagram showing a typical experiment conducted with a single-layer leaf spring. FIG. 2B is a schematic diagram showing a typical experiment conducted with a three-layer leaf spring.

The leaf spring 8 shown in FIG. 2A is a single-layer leaf spring made of an acrylic material 8. It is 0.5 mm in thickness, 90 mm in length, and 20 mm in width. The width of this leaf spring 8 is equal to that of the flaw sensor 1. The acrylic plate having the above dimensions does not permanently deform even when it is bent with a curvature radius of 30 mm during the experiment.

On the other hand, the leaf spring 5 shown in FIG. 2B is a three-layer leaf spring made of three acrylic plates 10. These acrylic plates 10 are equal in thickness and width, but 90 mm, 60 mm, and 30 mm respectively in length.

The elastic body 3 has a thickness of 10 mm. The flaw sensor 1 has a thickness of 0.3 mm. The depth of the concave section of the pressure section 6 is 5 mm smaller than the total thickness of the flaw sensor 1 and elastic bodies 3, 5 (10.8 mm in FIG. 2A or 11.8 mm in FIG. 2B).

As shown in FIG. 2A, the eddy current flaw detection probe uses the pressure section 6 to press the flaw sensor 1 at the center of the leaf spring 8 via the elastic body 3 and leaf spring 8. Meanwhile, as shown in FIG. 2B, the eddy current flaw detection probe uses the pressure section 6 to press the flaw sensor 1 at the center of the leaf spring 5 via the elastic body 3 and leaf spring 5.

Pressure sensors are mounted at three points (A, B, and C) of a test piece 9 to measure the pressure distribution of the flaw sensor 1. Two different types of test piece 9 are used. One has a curvature radius of 30 mm, whereas the other has a curvature radius of 100 mm.

FIG. 3 shows an experiment result obtained when the single-layer leaf spring 8 was used. In FIG. 3, the vertical axis indicates the pressing force that is applied to the pressure sensors by the flaw sensor 1 (normalized at point A), whereas the horizontal axis indicates the positions of the three pressure sensors (at points A, B, and C).

The broken line 11 in the figure represents the characteristic of a curvature radius of 30 mm, whereas the solid line 12 represents the characteristic of a curvature radius of 100 mm. As is obvious from the obtained result, the pressing force sequentially decreases from point A through point B to point C. The obtained result also indicates that a small pressing force is applied to point C, which is positioned at an end of the leaf spring, when the curvature radius is 30 mm, and that virtually no pressing force is applied when the curvature radius is 100 mm. In other words, when the single-layer leaf spring is used to check for a flaw on the surface of a curve having a curvature radius of 100 mm, it is highly probable that a flaw sensor lift-off may occur at an end of the leaf spring.

On the other hand, FIG. 4 shows an experiment result obtained when the three-layer leaf spring 5 was used. The broken line 13 in the figure represents the characteristic of a curvature radius of 30 mm, whereas the solid line 14 represents the characteristic of a curvature radius of 100 mm. The obtained result indicates that the pressing force distribution is improved by the use of a multilayer leaf spring, and that the pressing force is applied to points A, B, and C no matter whether the curvature radius 30 mm or 100 mm. More specifically, even when the eddy current flaw detection probe 100 scans an inspection target whose curvature radius varies from 30 mm to 100 mm, the pressing force is applied to press the flaw sensor 1 against the inspection target. Therefore, the flaw sensor 1 can perform a scan without experiencing a lift-off. This makes it possible to achieve accurate flaw detection.

The lamination effect produced by the multilayer leaf spring for use in the eddy current flaw detection probe according to the present embodiment will now be described with reference to FIGS. 5, 6, and 7.

Figure 5:
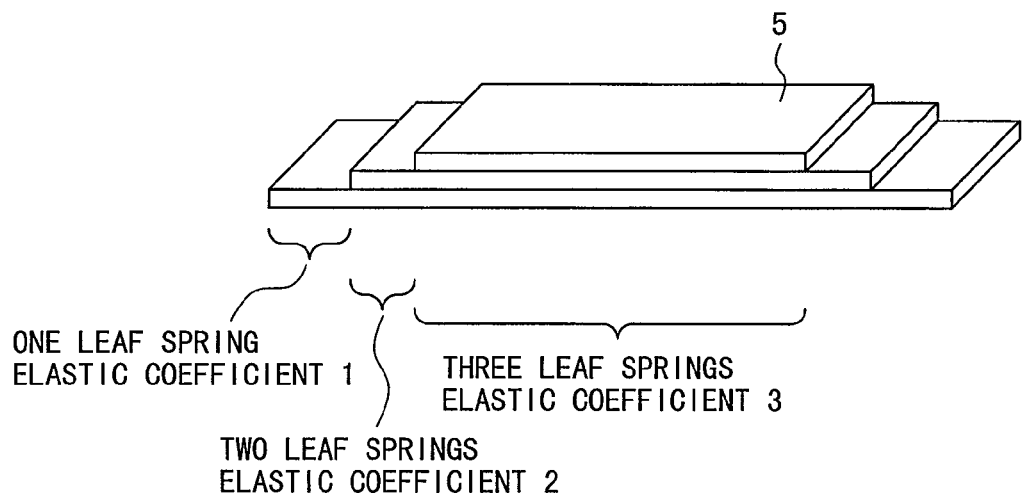
FIG. 5 is an illustration showing a lamination effect produced by the multilayer leaf spring for use in the eddy current flaw detection probe according to the first embodiment of the present invention.
Figure 6:
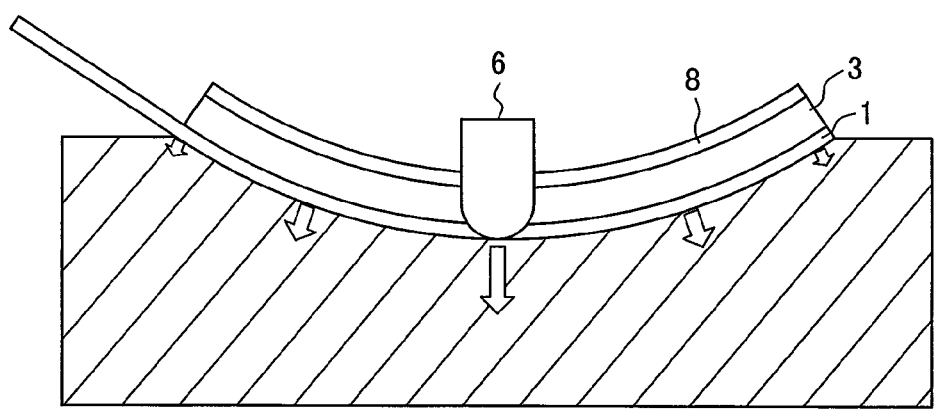
FIG. 6 is a comparative diagram that schematically shows how a single-layer leaf spring is pressed.
Figure 7:
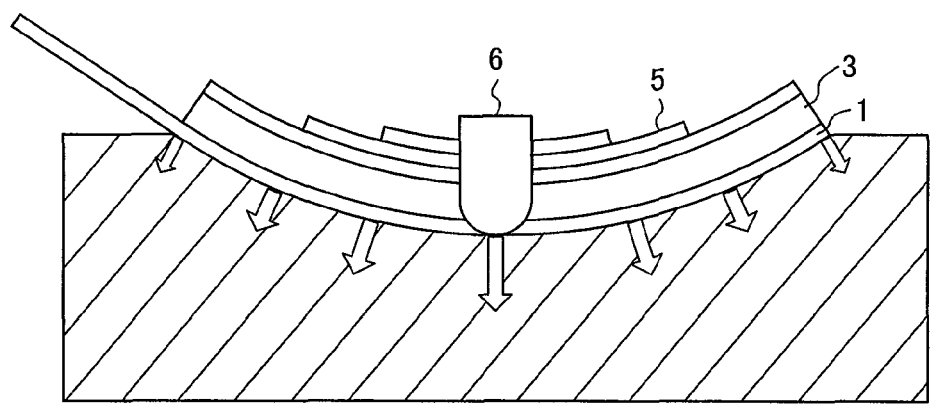
FIG. 7 is an illustration showing a lamination effect produced by the multilayer leaf spring for use in the eddy current flaw detection probe according to the first embodiment of the present invention.

FIGS. 5 and 7 are illustrations depicting the lamination effect produced by the multilayer leaf spring for use in the eddy current flaw detection probe according to the first embodiment of the present invention. FIG. 6 is a comparative diagram that schematically shows how a single-layer leaf spring is pressed.

FIG. 5 shows the elastic body 5, which is formed by stacking three leaf springs. The elastic body 5 has three different portions. From one end to the center, there are a portion having one leaf spring and elastic coefficient 1, a portion having two leaf springs and elastic coefficient 2, and a central portion having three leaf springs and elastic coefficient 3. Elastic coefficient 1<elastic coefficient 2<elastic coefficient 3. It means that the elastic body 5 is most unlikely to bend at the center. In other words, the elastic body 5, which is formed by stacking three leaf springs, has an elastic coefficient that varies in a longitudinal direction.

Consequently, when the center of the single-layer elastic body 8 is pressed as shown in FIG. 6, the pressing force drastically decreases toward both ends. On the other hand, when the center of the three-layer elastic body is pressed as shown in FIG. 7, the pressing force is more likely to work on both ends than during the use of the single-layer elastic body because the central portion does not readily bend. In addition, the three-layer elastic body can be used without deforming its leaf springs permanently due to the lamination effect.

As described above, the present embodiment varies the elastic coefficient by stacking a plurality of leaf springs. Therefore, even when the curvature of the surface of an inspection target varies, pressing force can be generated on the entire surface of the flaw sensor 1 simply by pressing the center of the leaf springs. This makes it possible to achieve accurate flaw detection without experiencing a lift-off. As a result, the inspection time can be reduced because it is not necessary to change the elastic body in accordance with a change in the curvature.

The configuration of an eddy current flaw detection probe according to a second embodiment of the present invention will now be described with reference to FIGS. 8 to 10.

Figure 8:
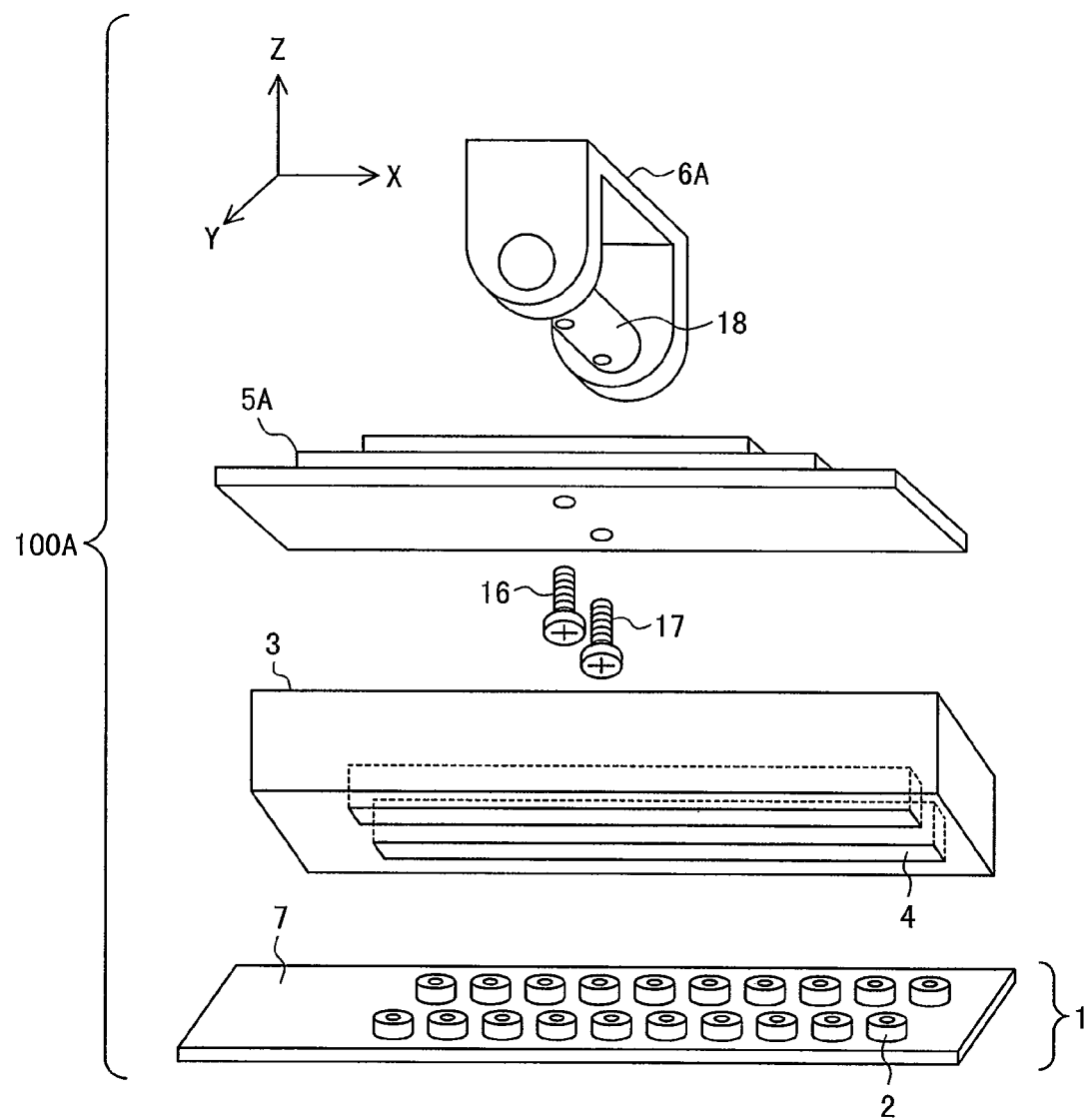
FIG. 8 is an exploded perspective view showing the overall configuration of an eddy current flaw detection probe according to a second embodiment of the present invention.

FIG. 8 is an exploded perspective view showing the overall configuration of the eddy current flaw detection probe according to the second embodiment of the present invention. FIG. 9 is a side view showing the eddy current flaw detection probe according to the second embodiment of the present invention. FIG. 10 is a side view showing how the eddy current flaw detection probe according to the second embodiment of the present invention is pressed against an inspection target. Like elements in FIGS. 1, 8, 9, and 10 are identified by the same reference numerals.

As shown in FIG. 8, the eddy current flaw detection probe 100A according to the present embodiment is effective in a situation where an inspection target having a curved surface in the longitudinal direction of the probe cannot be vertically pressed. This eddy current flaw detection probe 100A includes a flaw sensor 1, which faces the surface of an inspection target; elastic bodies 3, 5A, which bring the flaw sensor 1 into close contact with the inspection target; a rotary part 18, which rotates around an axis extending in Y-direction; and a pressure section 6A.

As is the case shown in FIG. 1, the flaw sensor 1 includes a flexible substrate 7, which is formed by stacking multiple layers of polyimide film or the like; and a plurality of coils 2, which are fastened to the non-inspection-target side of the flexible substrate 7 with adhesive or the like and unidirectionally arranged. In the present embodiment, the plurality of coils 2 are arranged to form two rows. The wiring (not shown) connected to each coil 2 is routed out by using a boundary between the layers of polyimide film.

As is the case shown in FIG. 1, one elastic body 3 is a sponge made, for instance, of polyurethane rubber and shaped like a rectangular parallelepiped. It forms coil receiver grooves 4 that can receive two rows of coils 2 on the side facing the flexible substrate 7. The other elastic body 5A is formed, for instance, by stacking three phosphor bronze plates or acrylic plates. The center of this elastic body 5A has two holes for accepting screws 16, 17 that fasten the elastic body 5A to the rotary part 18. The rotary part 18 is rotatably attached to the pressure section 6A and allowed to rotate around a Y-axis. The pressure section 6A is made, for instance, of Bakelite or aluminum and used to press the flaw sensor 1 via the elastic bodies 3, 5A and rotary part 18.

Figure 9:
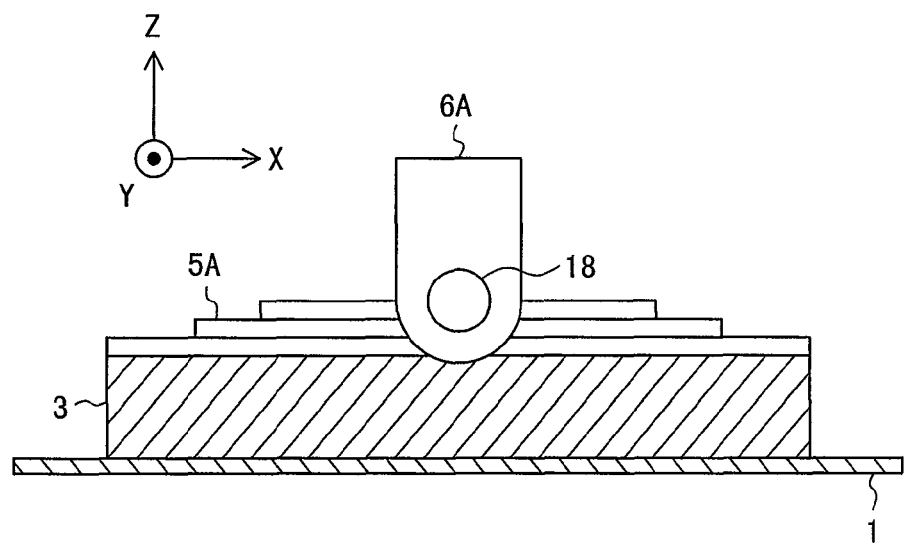
FIG. 9 is a side view showing the eddy current flaw detection probe according to the second embodiment of the present invention.
Figure 10:
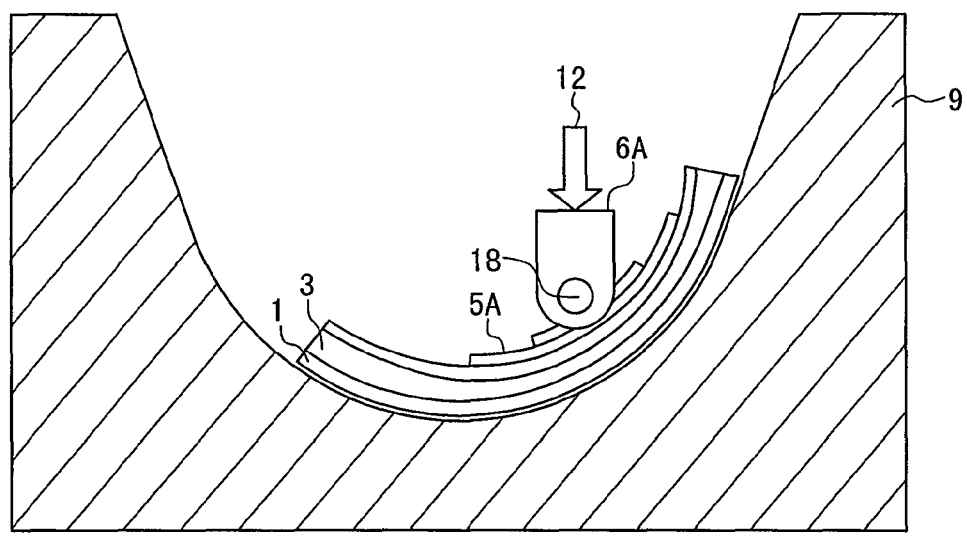
FIG. 10 is a side view showing how the eddy current flaw detection probe according to the second embodiment of the present invention is pressed against an inspection target.

FIG. 9 shows the eddy current flaw detection probe 100A as viewed in the Y-direction. The configuration shown in this figure allows the rotation mechanism of the rotary part 18 to rotate the flaw sensor 1 and elastic bodies 3, 5A around the Y-axis. The use of this rotation mechanism enables the flaw sensor 1 to rotate in such a manner as to naturally follow the gradient of the surface of the inspection target 9 and come into close contact with the curved surface of the inspection target 9 even when the surface of the inspection target 9 is not perpendicular to the pressure direction 12 of the pressure section as shown in FIG. 10.

As described above, the use of the eddy current flaw detection probe 100A according to the present embodiment makes it possible to bring the flaw sensor 1 into close contact with an inspection target even in a situation where the eddy current flaw detection probe 100 according to the first embodiment cannot vertically press the surface of the inspection target that may impair the contact between the flaw sensor 1 and inspection target.

Further, as leaf springs are stacked so as to vary the elastic coefficient, pressing force can be generated on the entire surface of the flaw sensor 1 simply by pressing the center of the leaf springs even when the curvature of the surface of an inspection target varies. This makes it possible to achieve accurate flaw detection without experiencing a lift-off. As a result, the inspection time can be reduced because it is not necessary to change the elastic body in accordance with a change in the curvature.

The configuration of an eddy current flaw detection probe according to a third embodiment of the present invention will now be described with reference to FIGS. 11 to 13.

Figure 11:
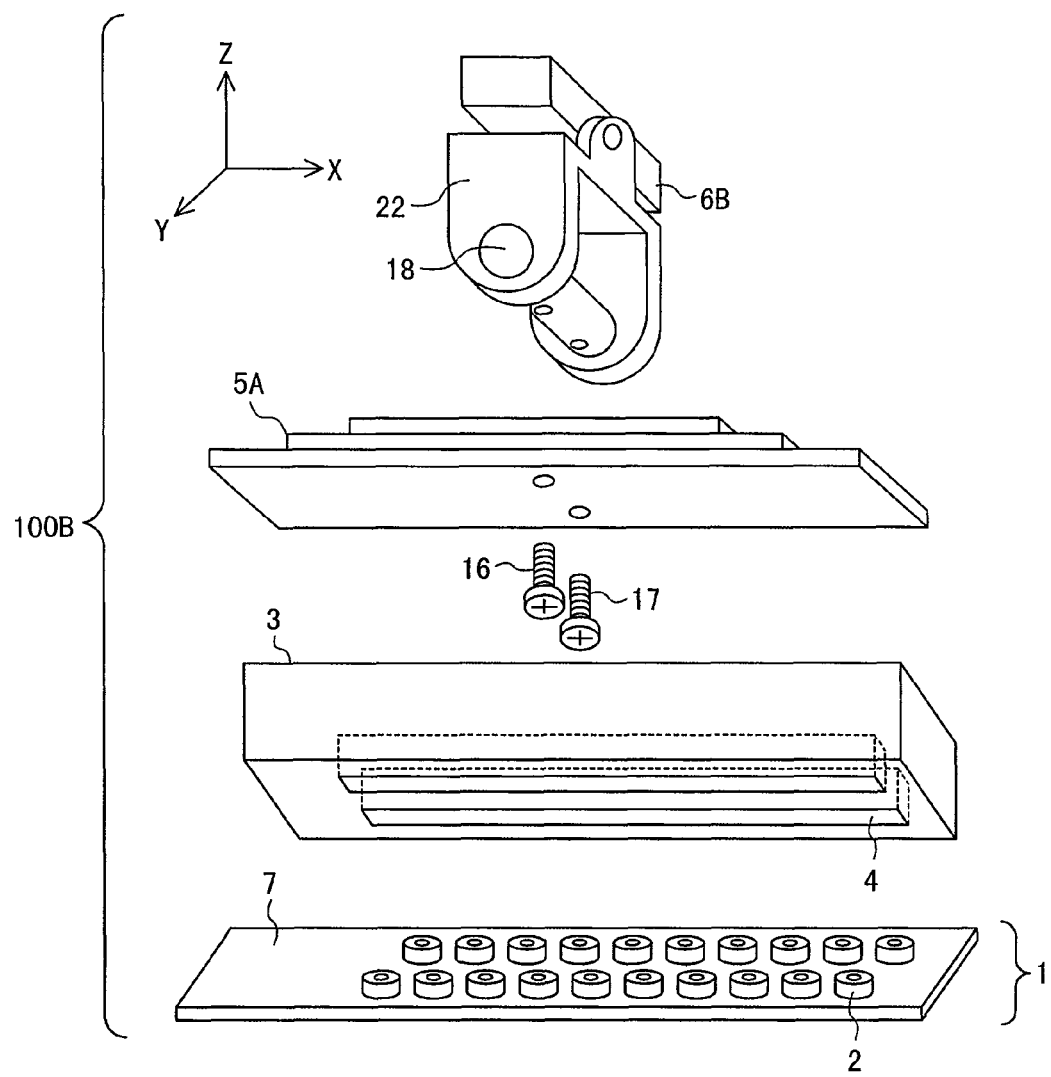
FIG. 11 is an exploded perspective view showing the overall configuration of an eddy current flaw detection probe according to a third embodiment of the present invention.

FIG. 11 is an exploded perspective view showing the overall configuration of the eddy current flaw detection probe according to the third embodiment of the present invention. FIG. 12 is a side view showing the eddy current flaw detection probe according to the third embodiment of the present invention. FIG. 13 is a side view showing how the eddy current flaw detection probe according to the third embodiment of the present invention is pressed against an inspection target. Like elements in FIGS. 1, 8, 11, 12, and 13 are identified by the same reference numerals.

As shown in FIG. 11, the eddy current flaw detection probe 100B according to the present embodiment is effective in a situation where an inspection target having a curved surface in the longitudinal and transverse directions of the probe cannot be vertically pressed by the pressure section. This eddy current flaw detection probe 100B includes a flaw sensor 1, which faces the surface of an inspection target; elastic bodies 3, 5A, which bring the flaw sensor 1 into close contact with the inspection target; a rotary part 18 that rotates around an axis extending in Y-direction; a rotary part 22 that rotates around an axis extending in X-direction; and a pressure section 6B.

As is the case shown in FIG. 1, the flaw sensor 1 includes a flexible substrate 7, which is formed by stacking multiple layers of polyimide film or the like; and a plurality of coils 2, which are fastened to the non-inspection-target side of the flexible substrate 7 with adhesive or the like and unidirectionally arranged. In the present embodiment, the plurality of coils 2 are arranged to form two rows. The wiring (not shown) connected to each coil 2 is routed out by using a boundary between the layers of polyimide film.

As is the case shown in FIG. 1, one elastic body 3 is a sponge made, for instance, of polyurethane rubber and shaped like a rectangular parallelepiped. It forms coil receiver grooves 4 that can receive two rows of coils 2 on the side facing the flexible substrate 7. The other elastic body 5A is formed, for instance, by stacking three phosphor bronze plates or acrylic plates. The center of this elastic body 5A has two holes for accepting screws 16, 17 that fasten the elastic body 5A to the rotary part 18. The rotary part 18 is attached to the rotary part 22 and allowed to rotate around a Y-axis. The rotary part 22 is attached to the pressure section 6B and allowed to rotate around an X-axis. The rotary parts 18, 22 and pressure section 6B are made, for instance, of Bakelite or aluminum and used to press the flaw sensor 1 via the elastic bodies 3, 5A and rotary parts 18, 22.

Figure 12:
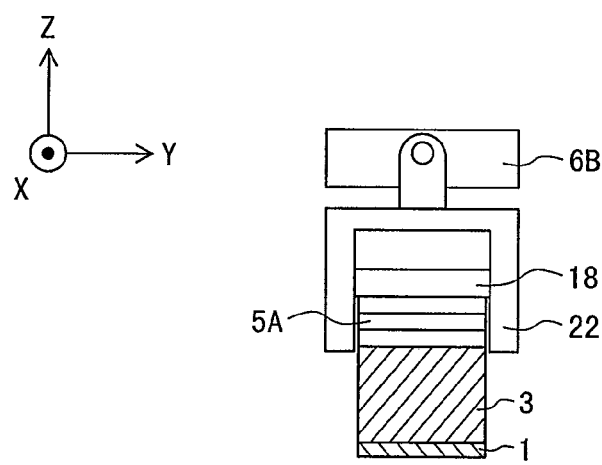
FIG. 12 is a side view showing the eddy current flaw detection probe according to the third embodiment of the present invention.

FIG. 12 shows the eddy current flaw detection probe 100B as viewed in the Y-direction. The configuration shown in this figure allows the rotation mechanisms of the rotary parts 18, 22 to rotate the flaw sensor 1 and elastic bodies 3, 5A around the X- and Y-axes.

Figure 13:
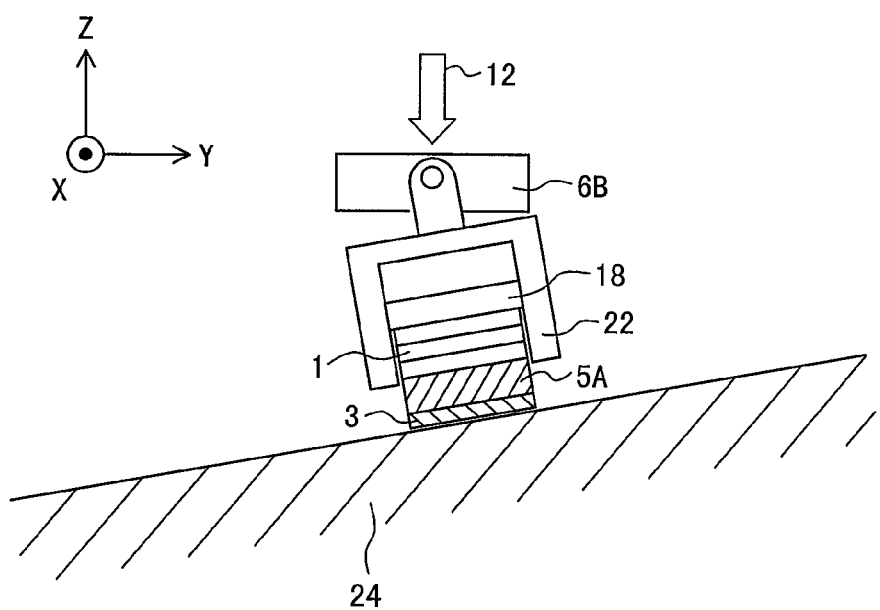
FIG. 13 is a side view showing how the eddy current flaw detection probe according to the third embodiment of the present invention is pressed against an inspection target.

The use of the eddy current flaw detection probe 100B described above makes it possible to bring the flaw sensor 1 into close contact with an inspection target even in a situation where the eddy current flaw detection probes 100, 100A according to the first or second embodiment cannot vertically press the surface of the inspection target that may impair the contact between the flaw sensor 1 and inspection target as shown in FIG. 13.

Further, as leaf springs are stacked so as to vary the elastic coefficient, pressing force can be generated on the entire surface of the flaw sensor 1 simply by pressing the center of the leaf springs even when the curvature of the surface of an inspection target varies. This makes it possible to achieve accurate flaw detection without experiencing a lift-off. As a result, the inspection time can be reduced because it is not necessary to change the elastic body in accordance with a change in the curvature.

The configuration of an eddy current flaw detection probe according to a fourth embodiment of the present invention will now be described with reference to FIGS. 14 to 16.

Figure 14:
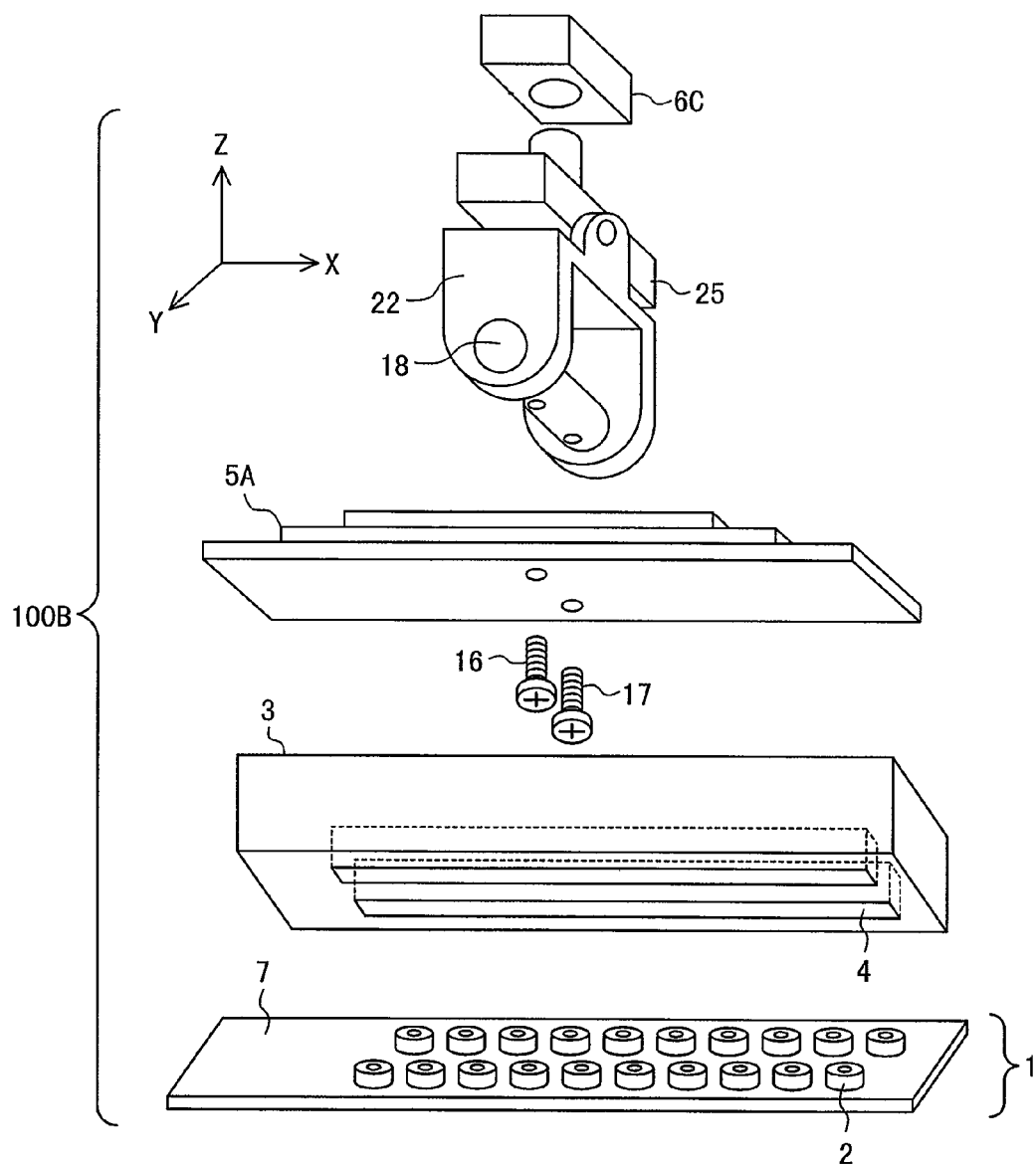
FIG. 14 is an exploded perspective view showing the overall configuration of an eddy current flaw detection probe according to a fourth embodiment of the present invention.

FIG. 14 is an exploded perspective view showing the overall configuration of the eddy current flaw detection probe according to the fourth embodiment of the present invention. FIG. 15 is a plan view showing the eddy current flaw detection probe according to the fourth embodiment of the present invention. FIG. 16 is a plan view showing how the eddy current flaw detection probe according to the fourth embodiment of the present invention is pressed against an inspection target. Like elements in FIGS. 1, 8, 11, 14, 15, and 16 are identified by the same reference numerals.

The eddy current flaw detection probe 100C shown in FIG. 14 is effective even when a flaw sensor 1 is improperly positioned relative to the curved surface of an inspection target. This eddy current flaw detection probe 100C includes a flaw sensor 1, which faces the surface of an inspection target; elastic bodies 3, 5A, which bring the flaw sensor 1 into close contact with the inspection target; a rotary part 18 that rotates around an axis extending in Y-direction; a rotary part 22 that rotates around an axis extending in X-direction; a rotary part 25 that rotates around an axis extending in Z-direction; and a pressure section 6C.

Figure 15:
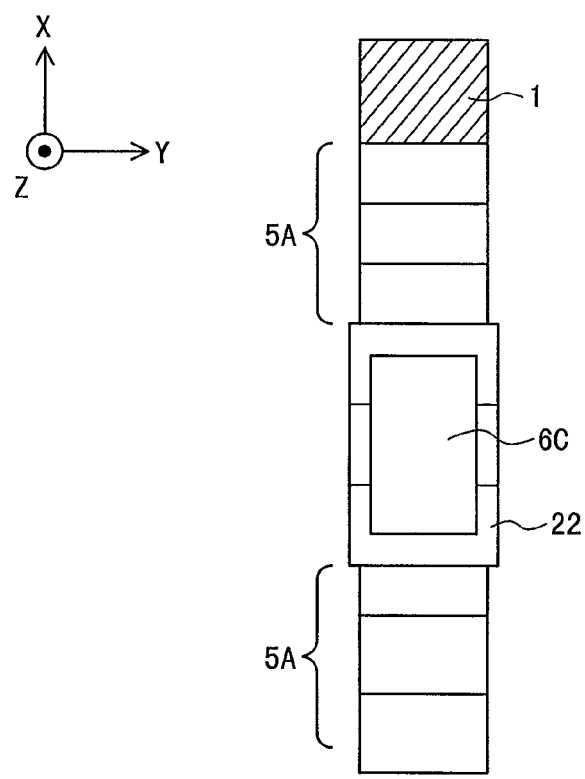
FIG. 15 is a plan view showing the eddy current flaw detection probe according to the fourth embodiment of the present invention.
Figure 16:
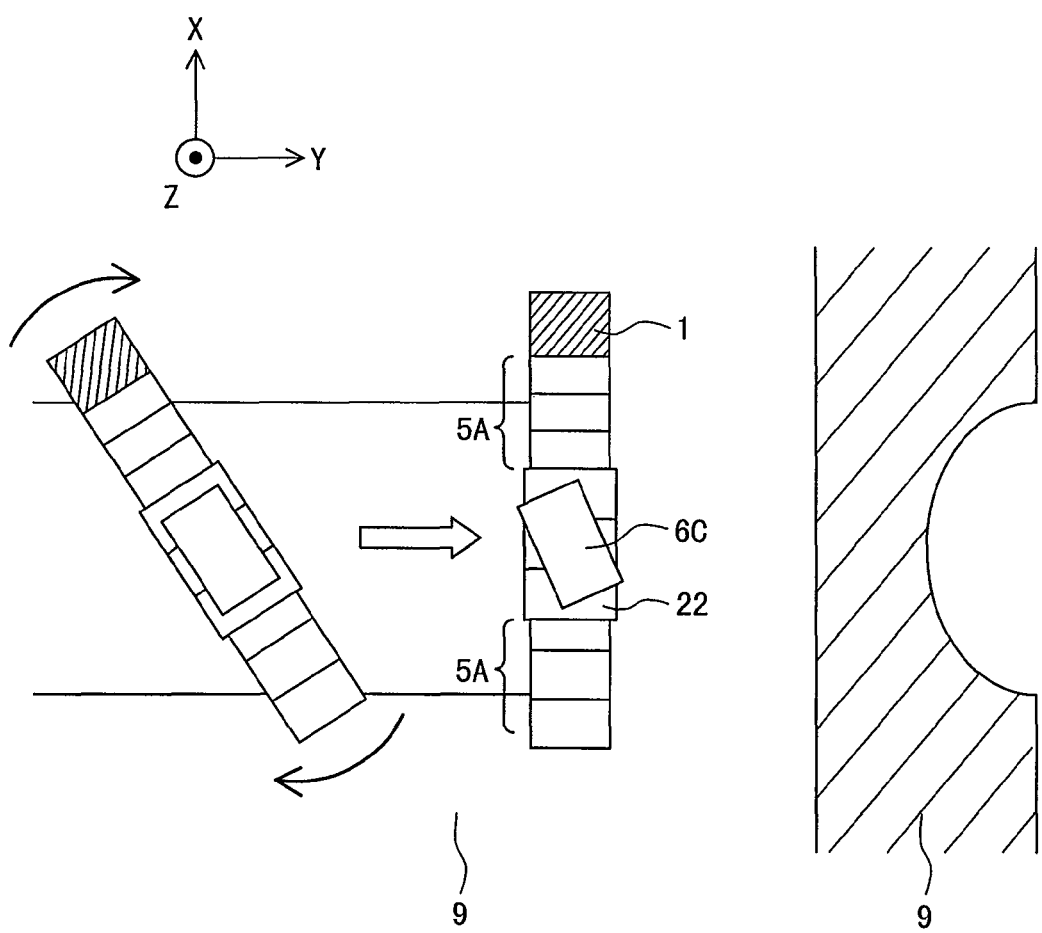
FIG. 16 is a plan view showing how the eddy current flaw detection probe according to the fourth embodiment of the present invention is pressed against an inspection target.

FIG. 15 shows the eddy current flaw detection probe 100B as viewed in the Z-direction. The configuration shown in this figure allows the rotation mechanisms of the rotary parts 18, 22 to rotate the flaw sensor 1 and elastic bodies 3, 5A around the X-, Y-, and Z-axes.

The use of the eddy current flaw detection probe 100B described above makes it possible to bring the flaw sensor 1 into close contact with an inspection target even in a situation where the flaw sensor 1 of the eddy current flaw detection probes 100, 100A, 100B according to the first, second, or third embodiment is improperly positioned relative to the curved surface of the inspection target that may impair the contact between the flaw sensor 1 and inspection target.

The flaw sensor 1 can inspect the whole row length of the coils 2 by performing a single scan. Therefore, the widest area can be inspected by performing a scan orthogonally to the length direction of the coil rows. If, for instance, the direction in which the curved surface of an inspection target is oriented is not orthogonal to the length direction of the coil rows of the flaw sensor 1 as shown in FIG. 16, the rotation mechanism that rotates around the Z-axis can make adjustments so that the posture of the flaw sensor 1 changes from a state shown at left to a state shown at right, which is indicated by an arrow. This makes it possible to conduct an extensive inspection of a curved surface with high efficiency.

Further, as leaf springs are stacked so as to vary the elastic coefficient, pressing force can be generated on the entire surface of the flaw sensor 1 simply by pressing the center of the leaf springs even when the curvature of the surface of an inspection target varies. This makes it possible to achieve accurate flaw detection without experiencing a lift-off. As a result, the inspection time can be reduced because it is not necessary to change the elastic body in accordance with a change in the curvature.

It should be noted that the eddy current flaw detection probes 100, 100A, 100B, and 100C are used in a gas or liquid. If the sponge made of polyurethane rubber, which forms the elastic body 3, contains sealed, independent air bubbles in a situation where the eddy current flaw detection probes 100, 100A, 100B, and 100C are used in a liquid, the pressure of the liquid compresses the air bubbles until they decrease in size. When the air bubbles are reduced in size, the sponge is no longer flexible. Consequently, the flaw sensor 1 cannot follow the surface shaped of an inspection target and fails to achieve accurate flaw detection. Therefore, when the eddy current flaw detection probes 100, 100A, 100B, and 100C are to be used in a liquid, the elastic body 3 should be made of a porous sponge that has no sealed air bubbles and allows the liquid to freely permeate it.

The foregoing description assumes that a three-layer leaf spring is used. However, the present invention is not limited to the use of a three-layer leaf spring. The number of leaf springs to be stacked may be changed depending on the shape of the curved surface of an inspection target. Further, the foregoing description assumes that the elastic bodies 4, 4A, 4B, and 4C are formed by a sponge made of polyurethane rubber. Alternatively, however, the elastic bodies 4, 4A, 4B, and 4C may be made, for instance, of a rubber material instead of a sponge.

The eddy current flaw detection probe 100A includes a rotation mechanism that rotates around the X-axis. The eddy current flaw detection probe 100B includes rotation mechanisms that rotate around the X- and Y-axes. The eddy current flaw detection probe 100C includes rotation mechanisms that rotate around the X-, Y-, and Z-axes. Alternatively, however, the probe may include the rotation mechanism(s) for one or two of the above three axes depending on the shape of the curved surface of an inspection target.

The configuration of an eddy current flaw detection probe according to a fifth embodiment of the present invention will now be described with reference to FIG. 17. The overall configuration of the eddy current flaw detection probe according to the fifth embodiment is the same as shown in FIG. 1.

Figure 17:
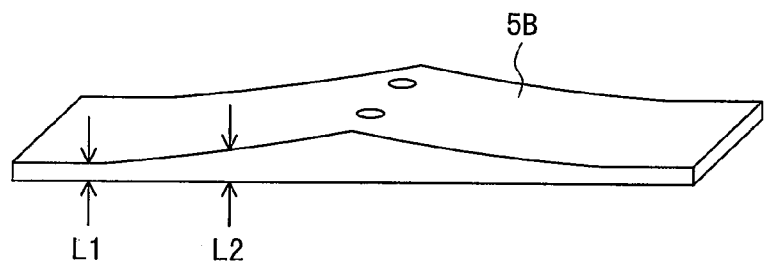
FIG. 17 is a perspective view showing the configuration of an elastic body for use in an eddy current flaw detection probe according to a fifth embodiment of the present invention.

FIG. 17 is a perspective view showing the configuration of an elastic body 5B for use in the eddy current flaw detection probe according to the fifth embodiment of the present invention.

The elastic body 5B may be a structure shown in FIG. 17. More specifically, the elastic body 5B may be designed so that plate thickness L1<plate thickness L2.

The configuration of an eddy current flaw detection probe according to a sixth embodiment of the present invention will now be described with reference to FIG. 18. The overall configuration of the eddy current flaw detection probe according to the sixth embodiment is the same as shown in FIG. 1.

Figure 18:
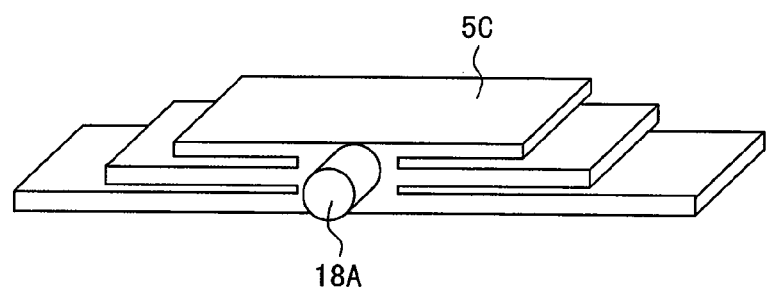
FIG. 18 is a perspective view showing the configuration of an elastic body for use in an eddy current flaw detection probe according to a sixth embodiment of the present invention.

FIG. 18 is a perspective view showing the configuration of an elastic body 5C for use in the eddy current flaw detection probe according to the sixth embodiment of the present invention.

As shown in FIG. 18, the elastic body 5C may be a structure that looks like a stack of three leaf springs and incorporates a rotary part 18A.

The use of the above structure eliminates the necessity of screwing the rotary part to the elastic body.

The configuration of an eddy current flaw detection probe according to a seventh embodiment of the present invention will now be described with reference to FIG. 19. The overall configuration of the eddy current flaw detection probe according to the seventh embodiment is the same as shown in FIG. 1.

Figure 19:
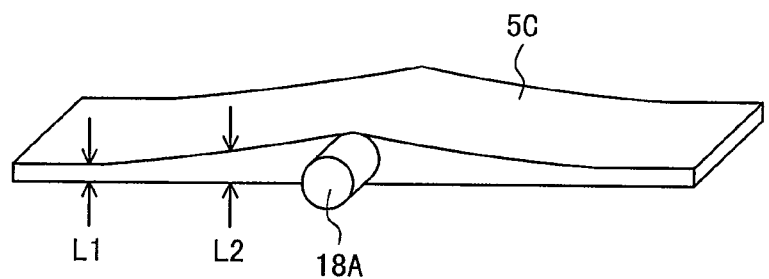
FIG. 19 is a perspective view showing the configuration of an elastic body for use in an eddy current flaw detection probe according to a seventh embodiment of the present invention.

FIG. 19 is a perspective view showing the configuration of an elastic body 5D for use in the eddy current flaw detection probe according to the seventh embodiment of the present invention.

As shown in FIG. 19, the elastic body 5D may be a structure that has different plate thicknesses (plate thickness L1<plate thickness L2) and incorporates a rotary part 18A.

The use of the above structure eliminates the necessity of screwing the rotary part to the elastic body.

The state of an inspection conducted with the eddy current flaw detection probes according to the foregoing embodiments of the present invention will now be described with reference to FIGS. 20 and 21.

Figure 20:
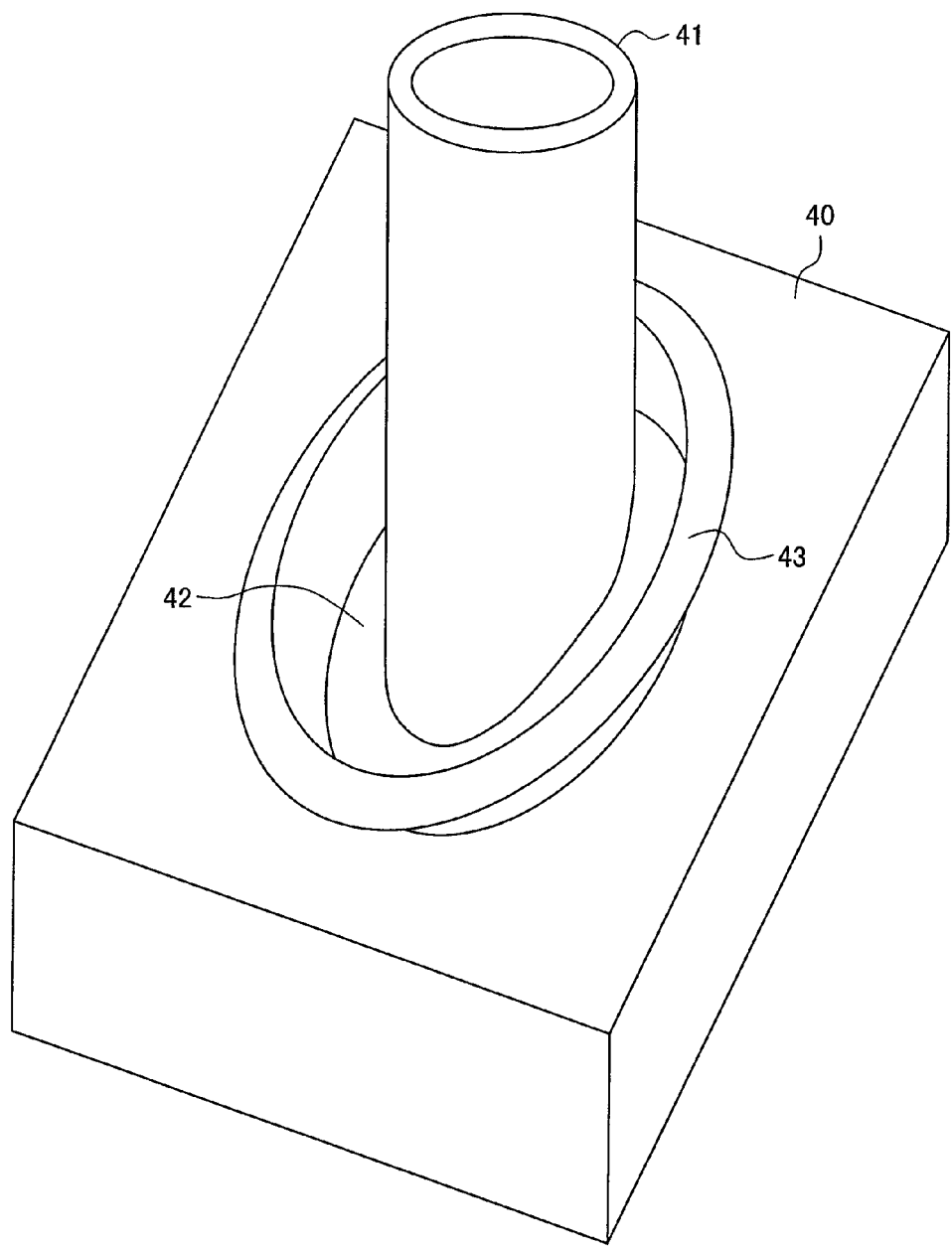
FIG. 20 is a perspective view exemplifying a weld zone that is to be inspected by the eddy current flaw detection probes according to the various embodiments of the present invention.

FIG. 20 is a perspective view exemplifying a weld zone that is to be inspected by the eddy current flaw detection probes according to the foregoing embodiments of the present invention.

Figure 21:
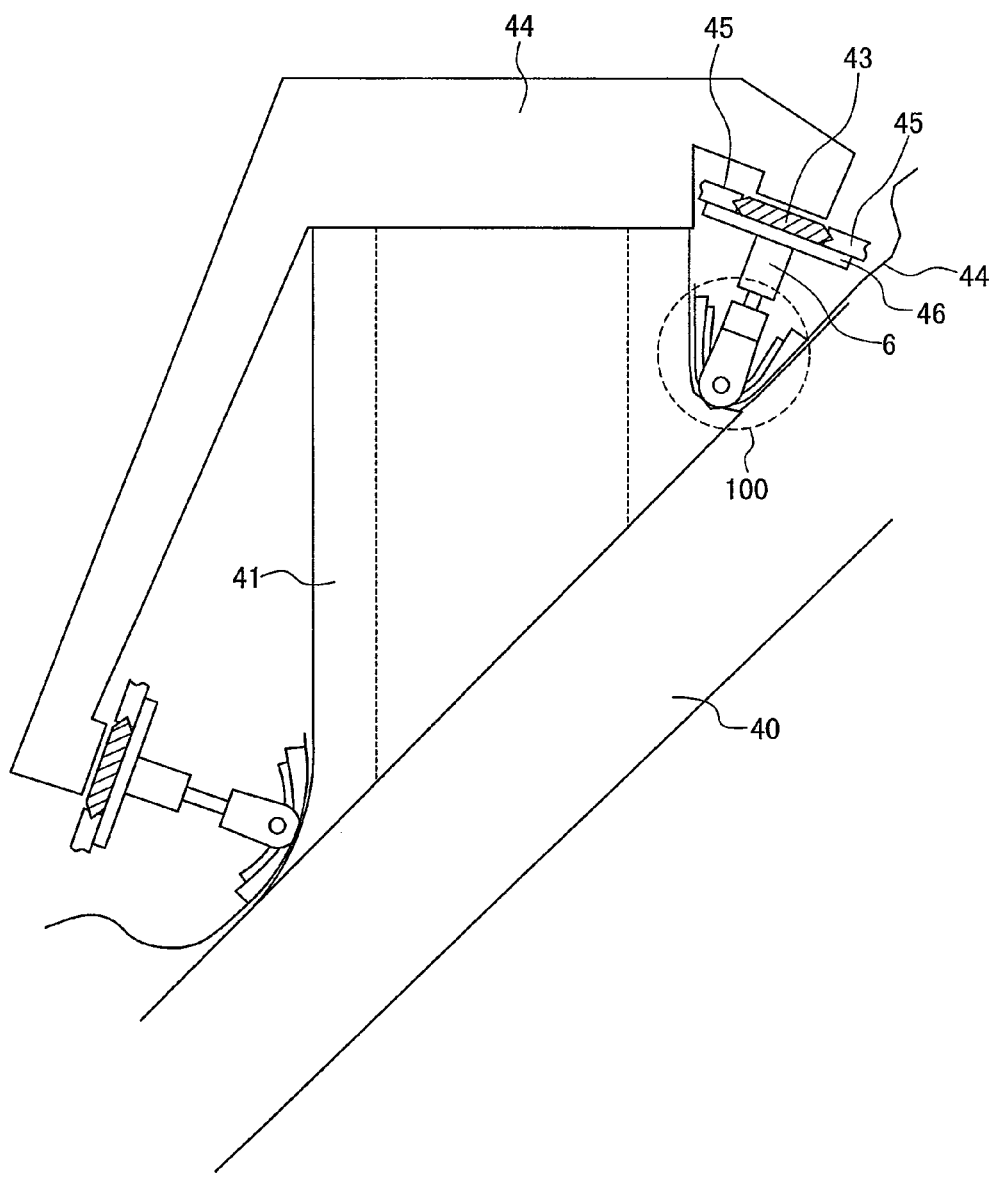
FIG. 21 is a side view showing the state of an inspection that is conducted with the eddy current flaw detection probes according to the various embodiments of the present invention.

FIG. 21 is a side view showing the state of an inspection that is conducted with the eddy current flaw detection probes according to the foregoing embodiments of the present invention.

When, for instance, a weld zone 42 for a pipe material 41 penetrating through the bottom of a nuclear reactor 40 as shown in FIG. 20 is to be inspected, a rail 43 designed to face the weld zone is provided. The rail 43 is secured with a jig 44 as shown in FIG. 21. A seat 46 on which an eddy current flaw detection probe 100 is to be mounted is secured to the rail 43 by wheels 45. The seat 46 can be steadily secured, for instance, by placing one wheel inside the rail and two wheels outside the rail although such is not indicated in the figure. The seat 46 is provided with an air cylinder 47, which presses the pressure section 6 of the eddy current flaw detection probe 100. While the air cylinder 47 presses the pressure section 6, the weld zone 42 can be inspected by moving the flaw sensor from a section having a small curvature shown at right in the figure to a section having a great curvature shown at left in the figure. In addition to the case described above, it is also possible to inspect a structure in the other cases where the curvature of the structure varies.

What is claimed is:

1. An eddy current flaw detection probe having a flexible substrate, which faces the surface of an inspection target, and a plurality of coils, which are fastened to the flexible substrate and sequentially selectable, the eddy current flaw detection probe comprising:
   a first elastic body which is positioned opposite the inspection target for the eddy current flaw detection probe, the first elastic body having an elastic coefficient that varies in a longitudinal direction;
   a second elastic body which is a porous body positioned between the flexible substrate and the first elastic body; and
   pressure means for pressing the first and second elastic bodies against the inspection target;
   wherein the pressure means includes a mechanism configured to rotatably support the first elastic body, including two or more elastic plates comprising the first elastic body, for rotation about an axis of rotation that is orthogonal to a longitudinal dimension of the first elastic body.

2. An eddy current flaw detection probe having a flexible substrate, which faces the surface of an inspection target, and a plurality of coils, which are fastened to the flexible substrate and sequentially selectable, the eddy current flaw detection probe comprising:
   a first elastic body which is positioned opposite the inspection target for the eddy current flaw detection probe, the first elastic body having an elastic coefficient that varies in a longitudinal direction;
   a second elastic body which is a porous body positioned between the flexible substrate and the first elastic body; and
   pressure means for pressing the first and second elastic bodies against the inspection target;
   wherein the pressure means includes a mechanism configured to rotatably support the first elastic body, including two or more elastic plates comprising the first elastic body, for rotation about an axis of rotation that is parallel to a longitudinal dimension of the first elastic body.

3. An eddy current flaw detection probe having a flexible substrate, which faces the surface of an inspection target, and a plurality of coils, which are fastened to the flexible substrate and sequentially selectable, the eddy current flaw detection probe comprising:
   a first elastic body which is positioned opposite the inspection target for the eddy current flaw detection probe, the first elastic body having an elastic coefficient that varies in a longitudinal direction;
   a second elastic body which is a porous body positioned between the flexible substrate and the first elastic body; and
   pressure means for pressing the first and second elastic bodies against the inspection target;
   wherein the pressure means includes a mechanism configured to rotate about an axis perpendicular to longitudinal dimensions of the first and second elastic bodies.

* * * * *